United States Patent
Ohno

(10) Patent No.: US 7,696,392 B2
(45) Date of Patent: Apr. 13, 2010

(54) PURIFICATION METHOD OF 1,1-DIFLUOROETHANE

(75) Inventor: Hiromoto Ohno, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 911 days.

(21) Appl. No.: 10/578,834

(22) PCT Filed: Nov. 4, 2004

(86) PCT No.: PCT/JP2004/016690

§ 371 (c)(1),
(2), (4) Date: May 10, 2006

(87) PCT Pub. No.: WO2005/044765

PCT Pub. Date: May 19, 2005

(65) Prior Publication Data

US 2007/0135617 A1 Jun. 14, 2007

Related U.S. Application Data

(60) Provisional application No. 60/524,888, filed on Nov. 26, 2003, provisional application No. 60/534,114, filed on Jan. 5, 2004.

(30) Foreign Application Priority Data

Nov. 10, 2003 (JP) ............................ 2003-379784
Dec. 24, 2003 (JP) ............................ 2003-428054

(51) Int. Cl.
  *C07C 17/38* (2006.01)
  *C07C 17/389* (2006.01)
(52) U.S. Cl. .................................................... 570/179
(58) Field of Classification Search ............... 570/179
    See application file for complete search history.

(56) References Cited

U.S. PATENT DOCUMENTS

| | | | |
|---|---|---|---|
| 3,862,995 A | 1/1975 | Martens et al. | |
| 4,906,796 A | 3/1990 | Yates | |
| 4,950,816 A | 8/1990 | Tung et al. | |
| 5,233,107 A * | 8/1993 | Jansen | 570/179 |
| 5,396,001 A | 3/1995 | Pennetreau | |
| 5,585,529 A * | 12/1996 | Corbin et al. | 570/179 |
| 5,626,725 A | 5/1997 | Balthasart et al. | |
| 6,274,782 B1 | 8/2001 | Ohno et al. | |
| 6,428,720 B1 | 8/2002 | Roberts | |
| 2001/0017364 A1 * | 8/2001 | Takemasa | 252/67 |
| 2002/0007099 A1 | 1/2002 | Anciaux et al. | |

FOREIGN PATENT DOCUMENTS

| | | |
|---|---|---|
| EP | 0 370 688 A1 | 5/1990 |
| EP | 0 693 469 A1 | 1/1996 |
| JP | 63-99535 A | 4/1988 |
| JP | 2001-247495 A | 9/2001 |
| WO | WO 96/40606 A1 | 12/1996 |
| WO | WO 01/83412 A2 | 11/2001 |

OTHER PUBLICATIONS

Golubev A N, et al:, "1,1-Difluoroethane", Chemical Abstracts+ Indexes, American Chemical Society. Columbus, US, vol. 1, No. 78, 1973, p. 308, XP002013161, ISSN: 0009-2258, abstract.
WPI World Patent Information Derwent, Derwent, GB PA—Electro Chemical IND CO L PN—JP47011726B B, 1973, XP002028123, abstract.

\* cited by examiner

*Primary Examiner*—Brian J Davis
(74) *Attorney, Agent, or Firm*—Sughrue Mion, PLLC

(57) ABSTRACT

Crude 1,1-difluoroethane containing at least one compound selected from the group consisting of unsaturated compounds each having two carbon atoms within the molecule and saturated chlorine-containing compounds each having two carbon atoms within the molecule is brought into contact with a zeolite and/or a carbonaceous adsorbent, or crude 1,1-difluoroethane containing hydrogen fluoride and, as impurities, at least one compound selected from the group consisting of unsaturated compounds each having two carbon atoms within the molecule is brought into contact with a fluorination catalyst in a gas phase state. High-purity 1,1-difluoroethane usable as a cryogenic refrigerant, or as an etching gas, can be produced in an industrially advantageous manner.

9 Claims, No Drawings

PURIFICATION METHOD OF 1,1-DIFLUOROETHANE

CROSS REFERENCE TO RELATED APPLICATIONS

This application is a 371 of PCT/JP04/16690 filed Nov. 4, 2004 claiming benefit of priority pursuant to 35 U.S.C. §119 (e)(1) of the filing dates of the Provisional Application 60/524,888 filed Nov. 26, 2003, and the Provisional Application 60/534,114 filed Jan. 5, 2004, pursuant to 35 U.S.C. §111(b).

TECHNICAL FIELD

The present invention relates to a purification method, a production process, and a use of, 1,1-difluoroethane.

BACKGROUND ART

The 1,1-difluoroethane ($CH_3CHF_2$) is attracting attention as, for example, a cryogenic refrigerant or an etching gas.

As for the production and purification methods for 1,1-difluoroethane, the following methods have been conventionally used, for example, (1) a method of reducing chlorinated fluorinated hydrocarbon with hydrogen in the presence of a catalyst (see, Japanese Unexamined Patent Publication No. 7-126197 (JP-A-7-126197)), and (2) a method of fluorinating chloroethylene ($CH_2=CHCl$), 1-chloro-1-fluoroethane or the like in a gas phase by using a fluorination catalyst and reacting unsaturated compounds contained as impurities with an oxide of copper, cobalt, silver, magnesium or the like (see, European Unexamined Patent Publication No. 0370688).

For example, $CH_3CHF_2$ (HFC-152a) produced by a method of reacting 1,1-dichloroethane with hydrogen fluoride in the presence of a fluorination catalyst, which is a general production process, or the method of (1) above contains various impurities such as saturated compounds of hydrocarbons (HC), hydrochlorocarbons (HCC), chlorofluorocarbons (CFC), hydrochlorofluorocarbons (HCFC) and hydrofluorocarbons (HFC) or unsaturated compounds.

To obtain high-purity $CH_3CHF_2$, these impurities must be removed as far as possible. In particular, chlorine-containing compounds such as hydrochlorocarbon, chlorofluorocarbon and hydrochlorofluorocarbon must, even when difficult to separate by normal distillation, be purified to elevate the purity not only for obtaining a high-purity product but also from the aspect of preventing depletion of the ozone layer. Among those impurities, some compounds form an azeotropic or azeotrope-like mixture with $CH_3CHF_2$ and therefore, their separation from $CH_3CHF_2$ is very difficult.

For example, regarding the purification of impurities such as 1,1,1,2-tetrafluoroethane ($CF_3CH_2F$) and pentafluoroethane ($CF_3CHF_2$), which are important as refrigerants, a purification method of removing these compounds by extractive distillation or by dehalogenating hydrogenation using hydrogen in the presence of a catalyst is known. However, the purification method by extractive distillation requires a plurality of expensive facilities such as a distillation tower and this disadvantageously incurs high equipment cost and the like. Also, the purification method using hydrogen has a problem such as high equipment cost and short catalyst life because of the use of a combustible. Furthermore, hydrogen chloride is produced and therefore, the life of the catalyst is shortened.

For the purification of 1,1-difluoroethane, for example, the method of (2) above has been proposed but, in the method of (2), a step of removing the oxidized product is necessary.

DISCLOSURE OF INVENTION

Under these circumstances, an object of the present invention is to provide an industrially advantageous method for producing high-purity 1,1-difluoroethane which can be used as a cryogenic refrigerant or an etching gas.

Means to Solve the Problems

As a result of intensive investigations to solve the above-described problems, the present inventors have found that the above-described object can be attained by using a method of bringing crude 1,1-difluoroethane containing at least one compound selected from the group consisting of unsaturated compounds each having two carbon atoms within the molecule and saturated chlorine-containing compounds each having two carbon atoms within the molecule, into contact with an adsorbent comprising a zeolite having an average pore size of 3 to 6 Å and a silica/aluminum ratio of 2.0 or less and/or a carbonaceous adsorbent having an average pore size of 3.5 to 6 Å to reduce the content of the compound contained as an impurity in the crude 1,1-difluoroethane. The present invention has been accomplished based on this finding.

The present inventors also have found that the above-described object can be attained by using a method of bringing crude 1,1-difluoroethane, containing hydrogen fluoride and, as impurities, at least one compound selected from the group consisting of unsaturated compounds each having two carbon atoms within the molecule, into contact with a fluorination catalyst in a gas phase state to reduce the content of unsaturated compounds each having two carbon atoms within the molecule. The present invention has been accomplished based on this finding.

Therefore, the present invention provides a purification method, a production process and a use of 1,1-difluoroethane, described in the following [1] to [19].

[1] A method for purifying 1,1-difluoroethane, comprising bringing crude 1,1-difluoroethane containing at least one compound selected from the group consisting of unsaturated compounds each having two carbon atoms within the molecule and saturated chlorine-containing compounds each having two carbon atoms within the molecule, into contact with an adsorbent comprising a zeolite having an average pore size of 3 to 6 Å and a silica/aluminum ratio of 2.0 or less and/or a carbonaceous adsorbent having an average pore size of 3.5 to 6 Å to reduce the content of the compound contained as an impurity in the crude 1,1-difluoroethane.

[2] The method for purifying 1,1-difluoroethane as described in [1] above, wherein the unsaturated compound having two carbon atoms within the molecule is at least one compound selected from the group consisting of ethylene, fluoroethylene, vinyl chloride and vinylidene chloride.

[3] The method for purifying 1,1-difluoroethane, as described in [1] above, wherein the saturated chlorine-containing compound having two carbon atoms within the molecule is at least one compound selected from the group consisting of dichloroethane, 1-chloro-1-fluoroethane and 2-chloro-1,1,1,2-tetrafluoroethane.

[4] The method for purifying 1,1-difluoroethane as described in any one of [1] to [3] above, wherein the total content of the compounds contained as impurities in the crude 1,1-difluoroethane is 0.1 vol % or less.

[5] The method for purifying 1,1-difluoroethane as described in any one of [1] to [4] above, wherein the pressure for bringing the crude 1,1-difluoroethane into contact with the adsorbent is 1 MPa or less.

[6] The method for purifying 1,1-difluoroethane as described in [1] to [5] above, wherein the total content of the compounds contained as impurities in the purified 1,1-difluoroethane is 100 vol ppm or less.

[7] The method for purifying 1,1-difluoroethane as described in any one of [1] to [6] above, wherein the total content of unsaturated compounds each having two carbon atoms within the molecule, contained as impurities in the purified 1,1-difluoroethane is 50 vol ppm or less.

[8] The method for purifying 1,1-difluoroethane as described in any one of [1] to [7] above, wherein the total content of saturated chlorine-containing compounds each having two carbon atoms within the molecule, contained as impurities in the purified 1,1-difluoroethane is 50 vol ppm or less.

[9] The method for purifying 1,1-difluoroethane as described in any one of [1] to [8] above, wherein the crude 1,1-difluoroethane is obtained by a method comprising the following steps (1) to (3):

(1) a step of reacting 1,1-dichloroethane with hydrogen fluoride in the presence of a fluorination catalyst to obtain mainly 1,1-difluoroethane, (2) a step of separating hydrogen fluoride, 1,1-dichloroethane and 1-chloro-1-fluoroethane from the product containing 1,1-difluoroethane obtained in the step (1) and circulating the separated compounds to a reaction step, and (3) a step of separating, by distillation, hydrogen chloride and/or 1,1-difluoroethane from the product containing 1,1-difluoroethane obtained in the step (1).

[10] A 1,1-difluoroethane product, which is 1,1-difluoroethane purified by using the method described in any one of [1] to [9] above, wherein the water content is 5 vol ppm or less.

[11] A 1,1-difluoroethane product, which is 1,1-difluoroethane purified by using the method described in any one of [1] to [9] above, wherein the hydrogen fluoride content is 2 vol ppm or less.

[12] A refrigerant comprising the 1,1-difluoroethane product described in [10] or [11].

[13] An etching gas comprising the 1,1-difluoroethane product described in [10] or [11].

[14] A method for purifying 1,1-difluoroethane, comprising bringing crude 1,1-difluoroethane, containing hydrogen fluoride and, as impurities, at least one compound selected from the group consisting of unsaturated compounds each having two carbon atoms within the molecule, into contact with a fluorination catalyst in a gas phase state to reduce the content of the unsaturated compounds each having two carbon atoms within the molecule.

[15] The method for purifying 1,1-difluoroethane as described in [14] above, wherein the unsaturated compound having two carbon atoms within the molecule is selected from ethylene, fluoroethylene, chlorofluoroethylene, vinyl chloride and vinylidene dichloride.

[16] The method for purifying 1,1-difluoroethane as described in [14] or [15] above, wherein the total content of the unsaturated compounds each having two carbon atoms within the molecule, contained as impurities in the crude 1,1-difluoroethane, is 1 vol % or less.

[17] The method for purifying 1,1-difluoroethane as described in any one of [14] to [16] above, wherein the fluorination catalyst contains at least one element selected from the group consisting of Cu, Mg, Zn, Pb, Cr, Al, In, Bi, Co and Ni and the contact temperature is from 100 to 350° C.

[18] A process for producing 1,1-difluoroethane, comprising the following steps:

(1) a step of reacting 1,1-dichloroethane with hydrogen fluoride in the presence of a fluorination catalyst to obtain a product containing mainly 1,1-difluoroethane, (2) a step of introducing the product containing mainly 1,1-difluoroethane obtained in the step (1) into a first distillation tower, separating mainly hydrogen chloride from the top, separating a side-cut fraction mainly comprising 1,1-difluoroethane and containing a slight amount of hydrogen fluoride from the middle portion, separating mainly hydrogen fluoride, 1,1-difluoroethane and 1-chloro-1-fluoroethane from the bottom, and circulating the bottom product to the reaction step, and (3) a step of bringing the side-cut fraction (crude 1,1-difluoroethane) obtained in the step (2) into contact with a fluorination catalyst in a gas phase state.

[19] A process for producing 1,1-difluoroethane, comprising the following steps:

(1) a step of reacting 1,1-dichloroethane with hydrogen fluoride in the presence of a fluorination catalyst to obtain a product containing mainly 1,1-difluoroethane, (2) a step of introducing the product containing mainly 1,1-difluoroethane obtained in the step (1) into a first distillation tower, separating mainly hydrogen chloride from the top, and separating mainly hydrogen fluoride, 1,1-dichloroethane, 1,1-dichloroethane and 1-chloro-1-fluoroethane from the bottom, (3) a step of introducing the bottom fraction obtained in the step (2) into a second distillation tower, separating crude 1,1-difluoroethane containing mainly hydrogen fluoride from the top, separating mainly hydrogen fluoride, 1,1-dichloroethane and 1-chloro-1-fluoroethane from the bottom, and circulating the bottom product to the reaction step, (4) a step of bringing the crude 1,1-difluoroethane containing mainly hydrogen fluoride, which is the top fraction obtained in the step (3), into contact with a fluorination catalyst in a gas phase state, and (5) a step of recovering hydrogen fluoride from the reactant obtained in the step (4).

According to the present invention, high-purity 1,1-difluoroethane can be efficiently produced by a simple and easy method, and the resulting purified 1,1-difluoroethane can be used as a cryogenic refrigerant or an etching gas.

BEST MODE FOR CARRYING OUT THE INVENTION

Preferred embodiments of the present invention are described in detail below.

As described above, with respect to the production method of $CH_3CHF_2$, for example, (1) a method of reducing a chlorinated fluorinated hydrocarbon with hydrogen in the presence of a catalyst, and (2) a method of fluorinating 1,1-dichloroethane, 1-chloro-1-fluoroethane or the like in a gas phase by using a fluorination catalyst are known. In $CH_3CHF_2$ produced by using these methods, impurities difficult to separate from $CH_3CHF_2$ are contained even when a generally employed operation for purification, such as distillation, is performed. Examples of these impurities include saturated compounds of hydrocarbons (HC), hydrochlorocarbons (HCC), chlorofluorocarbons (CFC), hydrochlorofluorocarbons (HCFC) and hydrofluorocarbons (HFC) or unsaturated compounds. These impurities must be removed as much as possible to obtain a high-purity product.

The purification method of 1,1-difluoroethane of the present invention is characterized in that crude 1,1-difluoroethane containing at least one compound selected from the group consisting of unsaturated compounds each having two carbon atoms within the molecule and saturated chlorine-containing compounds each having two carbon atoms within the molecule is brought into contact with an adsorbent comprising a zeolite having an average pore size of 3 to 6 Å and a silica/aluminum ratio of 2.0 or less and/or a carbonaceous adsorbent having an average pore size of 3.5 to 6 Å to reduce the content of the compound contained as an impurity in the crude 1,1-difluoroethane.

Examples of the unsaturated compounds each having two carbon atoms within the molecule, contained as impurities in the crude 1,1-difluoroethane include at least one compound selected from the group consisting of ethylene, fluoroethylene, vinyl chloride and vinylidene chloride. Examples of the saturated chlorine-containing compounds each having two carbon atoms within the molecule include at least one compound selected from the group consisting of dichloroethane, 1-chloro-1-fluoroethane and 2-chloro-1,1,1,2-tetrafluoroethane. The crude 1,1-difluoroethane containing these impurities is difficult to purify only by a known distillation operation and the present inventors have made further studies, for example, by changing the kind of adsorbent or the adsorption conditions in the light of polarity and pore size of the adsorbent.

As a result, it has been found that the above-described impurities can be selectively adsorbed and removed by contacting these impurities with a zeolite having an average pore size of 3 to 6 Å and a silica/aluminum ratio (Si/Al ratio) of 2.0 or less. Even when the silica/aluminum ratio is 2.0 or less, if the average pore size of the zeolite is less than 3 Å or exceeds 6 Å, the effect of decreasing the impurities is not obtained. Also, even when the average pore size is in the range from 3 to 6 Å, if the silica/aluminum ratio of the zeolite exceeds 2.0, the effect of decreasing the impurities is not obtained.

It has been also found that the above-described impurities can be selectively adsorbed and removed by contacting these impurities with a carbonaceous adsorbent (for example, molecular sieving carbon) having an average pore size of 3.5 to 6 Å. If the average pore size of the carbonaceous adsorbent used is less than 3.5 Å or exceeds 6 Å, the effect of decreasing the impurities is not obtained. For example, an activated carbon having an average pore size of about 35 Å, which is generally used, is known to have a strong adsorbing ability, but this cannot provide an effect of decreasing those impurities.

The above-described zeolite and carbonaceous adsorbent may be used individually or both may be used in combination at an arbitrary ratio.

The total content of those impurities contained as impurities in the crude 1,1-difluoroethane is preferably 0.1 vol % or less, more preferably 0.05 vol %. If the total content of the impurities exceeds 0.1 vol %, the amount of the adsorbent used increases to disadvantageously cause loss of 1,1-difluoroethane or elevation of the equipment cost or the like.

In the purification method of 1,1-difluoroethane of the present invention, the method for contacting the crude 1,1-difluoroethane containing those impurities with the adsorbent is not particularly limited and, for example, these may be contacted either in a gas phase or in a liquid phase, but the method of contacting in a liquid phase is efficient and preferred. For contacting these in a liquid phase, a known method such as batch system or continuous system can be used. For example, a method where two units of a fixed bed-system adsorption tower are provided and when one adsorption tower reaches saturated adsorption, this tower is changed over and regenerated can be used. The pressure for bringing the crude 1,1-difluoroethane into contact with the adsorbent is preferably 1 MPa or less. If the pressure exceeds 1 MPa, the equipment cost increases and this is not preferred.

The total content of the compounds contained as impurities in the 1,1-difluoroethane obtained by treating and purifying crude 1,1-difluoroethane as described above is 100 vol ppm or less, and a high-purity product can be obtained. The total content of unsaturated compounds each having two carbon atoms within the molecule, contained in the purified 1,1-difluoroethane is 50 vol ppm or less, and the total content of saturated chlorine-containing compounds each having two carbon atoms within the molecule, contained in the purified 1,1-difluoroethane is also 50 vol ppm or less. In other words, the purity of the purified 1,1-difluoroethane is 99.99 vol % or more.

The crude 1,1-difluoroethane is preferably crude 1,1-difluoroethane obtained by a method comprising:

(1) a step of reacting 1,1-dichloroethane with hydrogen fluoride in the presence of a fluorination catalyst to obtain mainly 1,1-difluoroethane, (2) a step of separating hydrogen fluoride, 1,1-difluoroethane and 1-chloro-1-fluoroethane from the product containing 1,1-difluoroethane obtained in the step (1) and circulating the separated compounds to a reaction step, and (3) a step of separating by distillation hydrogen chloride and 1,1-difluoroethane from the product containing 1,1-difluoroethane obtained in the step (1).

The step (1) may use a method of performing a fluorination reaction between the starting material, for example, 1,1-dichloroethane, and hydrogen fluoride in the presence of a fluorination catalyst to obtain crude 1,1-difluoroethane. The fluorination catalyst is preferably a supported or bulk catalyst mainly comprising a trivalent chromium oxide.

In the step (2), it is preferred to introduce the product containing 1,1-difluoroethane obtained in the step (1) into a first distillation tower, separate the top product (mainly hydrogen chloride and 1,1-difluoroethane) from hydrogen fluoride, 1,1-dichloroethane and 1-chloro-1-fluoroethane which are the main bottom products, and circulate the bottom products to the reaction step.

In the step (3), it is preferred to introduce the product containing 1,1-difluoroethane obtained in the step (1) into a first distillation tower, recover hydrogen chloride and 1,1-difluoroethane as top products, introduce these top products into a second distillation tower, distill mainly hydrogen chloride from the top, distill mainly 1,1-difluoroethane from the bottom, and then performed the above-described purification method.

More preferably, the acid content, mainly hydrogen fluoride, of the azeotropic fraction contained mainly in 1,1-difluoroethane which is the bottom product of a second distillation tower in the step (3), is washed with an aqueous alkali solution, water or the like, and still more preferably, a dehydration step is provided after the washing and thereafter the above-described purification method is performed.

As described above, the 1,1-difluoroethane after the purification has a purity of 99.99 vol %. In particular, the water content is 5 vol ppm or less and the hydrogen fluoride content (acid content) is 2 vol ppm or less.

The content of impurities contained in 1,1-difluoroethane can be measured by gas chromatography (GC) using TCD method or FID method or by gas chromatography-mass spectrometry (GC-MS). Also, the acid content can be measured by ion chromatography, and the water content can be measured by Karl Fischer's method or the like.

The high-purity 1,1-difluoroethane can be used as a refrigerant and, in addition, a mixed gas of the 1,1-difluoroethane with an inert gas (e.g., He, $N_2$, Ar), HCl, $O_2$, $H_2$ or the like can be used as an etching gas of the etching step in the process of producing a semiconductor device. In the process of producing a semiconductor device such as LSI, TFT and organic EL, a thin or thick film is formed by using a CVD method, a sputtering method or a vapor deposition method and etched to form a circuit pattern and, at this etching, a gas containing the above-described 1,1-difluoroethane can be used as the etching gas. The etching using the 1,1-difluoroethane can be performed under various dry etching conditions such as plasma etching and microwave etching.

The purification method of 1,1-difluoroethane of the present invention is characterized in that crude 1,1-difluoroethane containing hydrogen fluoride and, as impurities, at least one compound selected from the group consisting of unsaturated compounds each having two carbon atoms within the molecule is brought into contact with a fluorination catalyst in a gas phase state to reduce the content of the unsaturated compounds each having two carbon atoms within the molecule.

The production process of 1,1-difluoroethane of the present invention includes the following two methods.

The first method is a process comprising the following steps. That is, (1) 1,1-dichloroethane is reacted with hydrogen fluoride in the presence of, for example, a fluorination catalyst mainly comprising trivalent chromium oxide at a reaction temperature of 150 to 350° C. to obtain a product containing mainly 1,1-difluoroethane. The obtained product contains the objective 1,1-difluoroethane and additionally contains hydrogen chloride, unreacted hydrogen fluoride, 1,1-dichloroethane, 1-chloro-1-fluoroethane and impurities such as unsaturated or saturated compounds each having two carbon atoms. (2) The product containing mainly 1,1-difluoroethane, obtained in the step (1), is introduced into a first distillation tower and in the first distillation tower, hydrogen chloride which is a low boiling fraction is mainly separated from the top and recycled for another use, a side-cut fraction mainly comprising 1,1-difluoroethane and containing a slight amount of hydrogen fluoride and at least a part of saturated or unsaturated compounds each having two carbon atoms is separated and withdrawn from a stage upper than the middle portion of the distillation tower, and hydrogen fluoride, 1,1-dichloroethane and 1-chloro-1-fluoroethane which are a high boiling fraction are mainly separated and withdrawn from the bottom, circulated to the reaction step and recycled. (3) The side-cut fraction (crude 1,1-difluoroethane) separated and withdrawn in the step (2) contains a slight amount of hydrogen fluoride and, as impurities, unsaturated compounds each having two carbon atoms. In these compounds, compounds difficult to separate by a known distillation operation are contained as described above and, therefore, a fluorination reaction is performed in a gas phase state in the presence of a fluorination catalyst to convert unsaturated compounds each having two carbon atoms, which are impurities, into saturated compounds. The total amount of unsaturated compounds each having two carbon atoms within the molecule, which are impurities contained in the crude 1,1-difluoroethane, is preferably 1 vol % or less, more preferably 0.5 vol % or less. If the total amount of unsaturated compounds exceeds 1 vol %, this is not profitable because a large reactor, a high reaction temperature and the like are necessary. In the crude 1,1-difluoroethane, hydrogen chloride is sometimes contained, but the hydrogen chloride content is preferably 1 vol % or less. The fluorination catalyst brought into contact with the crude 1,1-difluoroethane is preferably a catalyst which is a compound of a metal belonging to Groups 1B, 2A, 2B, 4B, 5A, 5B, 6A, 7A and 8 of the Periodic Table and contains at least one element selected from the group consisting of Cu, Mg, Zn, Pb, Cr, Al, In, Bi, Co and Ni. For example, the catalyst is preferably (i) a supported or bulk catalyst mainly comprising trivalent chromium oxide or (ii) a supported catalyst containing Cr and at least one element selected from the group consisting of Cu, Mg, Zn, Pb, Al, In, Bi, Co and Ni. As for the raw material of such a catalyst, these metals and their oxides or salts may be used.

The support which can be used for the supported catalyst is alumina, fluorinated alumina or activated carbon.

As for the preparation of (i) a catalyst mainly comprising trivalent chromium oxide, for example, a basic substance such as ammonia is added dropwise to an aqueous solution of a metal salt of chromium to precipitate chromium hydroxide, the precipitate is washed, filtered and dried, and the resulting chromium hydroxide is shaped and then heat-treated in the presence of an inert gas such as nitrogen, whereby the catalyst can be obtained. In a pre-stage before use for reaction, the obtained catalyst is preferably subjected to, for example, a fluorination treatment (activation of catalyst) with hydrogen fluoride, which is a known method. The temperature at the contact with the catalyst is preferably 120 to 350° C., more preferably from 150 to 250° C. If the contact temperature exceeds 350° C., this disadvantageously shortens the life of catalyst or causes an increase in the kind or amount of by-product, or the like. The molar ratio of hydrogen fluoride to unsaturated compound is preferably 1 or more, and hydrogen fluoride may also be newly added and reacted.

The second method for the production of 1,1-difluoroethane is a process comprising the following steps. That is, (1) 1,1-dichloroethane is reacted with hydrogen fluoride in the presence of, for example, a fluorination catalyst mainly comprising trivalent chromium oxide at a reaction temperature of 150 to 350° C. to obtain a product containing mainly 1,1-difluoroethane. The obtained product contains the objective 1,1-difluoroethane and additionally contains unreacted hydrogen fluoride, hydrogen chloride, 1,1-dichloroethane, 1-chloro-1-fluoroethane and impurities such as unsaturated or saturated compounds each having two carbon atoms. (2) The product containing mainly 1,1-difluoroethane, obtained in the step (1), is introduced into a first distillation tower and in the first distillation tower, hydrogen chloride is mainly separated and withdrawn from the top and recycled for another use, and 1,1-difluoroethane, hydrogen fluoride, 1,1-dichloroethane, 1-chloro-1-fluoroethane and, as impurities, unsaturated or saturated compounds each having two carbon atoms are mainly separated and withdrawn from the bottom. (3) The bottom fraction obtained in the step (2) is introduced into a second distillation tower, crude 1,1-difluoroethane containing mainly a slight amount of hydrogen fluoride and unsaturated compounds each having two carbon atoms is separated and withdrawn from the top, and hydrogen fluoride, 1,1-dichloroethane and 1-chloro-1-fluoroethane are mainly separated and withdrawn from the bottom and circulated to the reaction step (1). (4) The top fraction obtained in the step (3) is subjected to a fluorination reaction treatment (purification) by using the same operations and conditions as in the above-described first method. (5) The reactant obtained in the step (4) contains unreacted hydrogen fluoride and therefore, the hydrogen fluoride must be recovered or removed from the reactant. The hydrogen fluoride is preferably recovered, for example, by a method using water or is preferably removed, for example, by a method of contacting it with an aqueous alkali solution or a purifying agent. It is preferred to perform recovery by water and recycling when the amount of unreacted hydrogen fluoride is large, and perform removal by the contact with an aqueous alkali solution or purifying agent when the amount is small. The purifying agent is preferably, for example, a purifying agent comprising a carbonaceous solid material and at least one member selected from alkali metal compounds, alkaline earth metal compounds, alkali metal salts of aluminic acid, and tetraalkylammonium salts. After the removal of hydrogen fluoride, the reactant mainly comprising 1,1-difluoroethane is, for example, brought into contact with a dehydrating agent such as zeolite and then introduced into a purification step where low boiling components (for example, oxygen, nitrogen and carbon dioxide) are separated, high boiling components (for example, 1-chloro-1-fluoroethane which is a reaction product) are subsequently removed, and high-purity 1,1-difluoroethane is recovered.

The present invention is described in greater detail below by referring to Examples and Comparative Examples, but the present invention is not limited to these Examples.

EXAMPLE 1

Preparation Example of Crude 1,1-Difluoroethane

Raw Material Example 1

1,1-Dichloroethane and hydrogen fluoride were introduced into a reactor filled with a catalyst (mainly comprising trivalent chromium oxide) and reacted at a temperature of 290° C. to produce a gas mainly comprising 1,1-difluoroethane, hydrogen chloride and unreacted hydrogen fluoride. Then, the hydrogen fluoride and hydrogen chloride were removed by distillation or the like to obtain crude 1,1-difluoroethane.

The obtained crude 1,1-difluoroethane was analyzed by gas chromatography and found to have the following composition.

| $CH_3CHF_2$ | 99.9461 | $CH_2=CH_2$ | 0.0018 |
|---|---|---|---|
| $CH_2=CHF$ | 0.0143 | $CH_3CHClF$ | 0.0013 |
| $CH_2=CHCl$ | 0.0261 | $CH_3CHClF$ | 0.0089 |
| $CH_2=CCl_2$ | 0.0012 | $CH_3CHCl_2$ | 0.0003 |

(unit: vol %)

Also, in the obtained crude 1,1-difluoroethane, the water content was 25 vol ppm and the hydrogen fluoride content was 6 vol ppm.

EXAMPLE 2

Preparation Example of Crude 1,1-Difluoroethane

Raw Material Example 2

The crude 1,1-difluoroethane obtained in Example 1 (Raw Material Example 1) was further subjected to distillation according to a known method to obtain crude 1,1-difluoroethane.

The obtained crude 1,1-difluoroethane was analyzed by gas chromatography and found to have the following composition.

| $CH_3CHF_2$ | 99.9666 | $CH_2=CH_2$ | 0.0006 |
|---|---|---|---|
| $CH_2=CHF$ | 0.0083 | $CH_3CHClF$ | 0.0011 |
| $CH_2=CHCl$ | 0.0178 | $CH_3CHClF$ | 0.0052 |
| $CH_2=CCl_2$ | 0.0004 | | |

(unit: vol %)

Also, in the obtained crude 1,1-difluoroethane, the water content was 23 vol ppm and the hydrogen fluoride content was 6 vol ppm.

EXAMPLE 3

A zeolite [Molecular Sieve 5A (produced by Union Showa K.K., average pore size: 4.2 Å, Si/Al ratio=1.0)] (20 g) was filled in a 200 ml-volume stainless steel-made cylinder and vacuum-dried. Then, about 80 g of the crude 1,1-difluoroethane of Raw Material Example 1 was filled while cooling the cylinder and occasionally stirred while keeping the temperature at −10° C. After about 20 hours, the liquid phase part was analyzed by gas chromatography and found to have the following composition.

| $CH_3CHF_2$ | 99.9925 | $CH_2=CH_2$ | 0.0001 |
|---|---|---|---|
| $CH_2=CHF$ | 0.0003 | $CH_3CHClF$ | 0.0007 |
| $CH_2=CHCl$ | 0.0021 | $CH_3CHClF$ | 0.0035 |
| $CH_2=CCl_2$ | 0.0007 | $CH_3CHCl_2$ | 0.0001 |

(unit: vol %)

Also, the water content in the 1,1-difluoroethane obtained after purification was analyzed by the Karl Fischer's method (water content analyzer) and found to be 3 vol ppm, and the hydrogen fluoride content was measured by ion chromatography and found to be 1 vol ppm.

EXAMPLE 4

A carbonaceous adsorbent [Molecular Sieving Carbon 4A (produced by Takeda Chemical Industries, Ltd., average pore size: 4 Å)] (20 g) was filled in a 200 ml-volume stainless steel-made cylinder and vacuum-dried. Then, about 80 g of the crude 1,1-difluoroethane of Raw Material Example 1 was filled while cooling the cylinder and occasionally stirred while keeping the temperature at −20° C. After about 18 hours, the liquid phase part was analyzed by gas chromatography and found to have the following composition.

| $CH_3CHF_2$ | 99.9975 | $CH_2=CH_2$ | 0.0001 |
|---|---|---|---|
| $CH_2=CHF$ | 0.0005 | $CH_3CHClF$ | 0.0002 |
| $CH_2=CHCl$ | 0.0011 | $CH_3CHClF$ | 0.0004 |
| $CH_2=CCl_2$ | 0.0001 | $CH_3CHCl_2$ | 0.0001 |

(unit: vol %)

EXAMPLE 5

A zeolite [Molecular Sieve 5A] (15 g) used in Example 3 and 15 g of a carbonaceous adsorbent [Molecular Sieving Carbon 4A] used in Example 4 were mixed and the mixture was filled in a 200 ml-volume stainless steel-made cylinder and vacuum-dried. Then, about 100 g of the crude 1,1-difluoroethane of Raw Material Example 2 was filled while cooling the cylinder and occasionally stirred while keeping the temperature at 10° C. After about 20 hours, the liquid phase part was analyzed by gas chromatography and found to have the following composition.

| $CH_3CHF_2$ | 99.9984 | $CH_2=CH_2$ | 0.0001 |
|---|---|---|---|
| $CH_2=CHF$ | 0.0003 | $CH_3CHClF$ | 0.0002 |
| $CH_2=CHCl$ | 0.0005 | $CH_3CHClF$ | 0.0004 |
| $CH_2=CCl_2$ | 0.0001 | | |

(unit: vol %)

Also, in the 1,1-difluoroethane obtained after purification, the water content was 4 vol ppm and the hydrogen fluoride content was 1 vol ppm.

EXAMPLE 6

A zeolite [Molecular Sieve 4A (produced by Union Showa K.K., average pore size: 3.5 Å, Si/Al ratio=1.0)] (20 g) was filled in a 200 ml-volume stainless steel-made cylinder and vacuum-dried. Then, about 80 g of the crude 1,1-difluoroethane of Raw Material Example 2 was filled while cooling the cylinder and occasionally stirred while keeping the temperature at 10° C. After about 20 hours, the liquid phase part was analyzed by gas chromatography and found to have the following composition.

| | | | |
|---|---|---|---|
| $CH_3CHF_2$ | 99.9911 | $CH_2=CH_2$ | 0.0002 |
| $CH_2=CHF$ | 0.0011 | $CH_3CHClF$ | 0.0010 |
| $CH_2=CHCl$ | 0.0032 | $CH_3CHClF$ | 0.0032 |
| $CH_2=CCl_2$ | 0.0002 | | |

(unit: vol %)

Comparative Example 1

A zeolite [Molecular Sieve 13X (produced by Union Showa K.K., average pore size: 10 Å, Si/Al ratio=1.2)] (20 g) was filled in a 200 ml-volume stainless steel-made cylinder and vacuum-dried. Then, about 80 g of the crude 1,1-difluoroethane of Raw Material Example 2 was filled while cooling the cylinder and occasionally stirred while keeping the temperature at 10° C. After about 20 hours, the liquid phase part was analyzed by gas chromatography and found to have the following composition.

| | | | |
|---|---|---|---|
| $CH_3CHF_2$ | 99.9711 | $CH_2=CH_2$ | 0.0006 |
| $CH_2=CHF$ | 0.0077 | $CH_3CHClF$ | 0.0009 |
| $CH_2=CHCl$ | 0.0146 | $CH_3CHClF$ | 0.0048 |
| $CH_2=CCl_2$ | 0.0003 | | |

(unit: vol %)

As apparent from these results, it is revealed that even when the Si/Al ratio is 2.0 or less, if the average pore size of zeolite exceeds 6 Å, the impurities cannot be selectively adsorbed and removed.

Comparative Example 2

An activated carbon [granular Shirosagi KL (produced by Takeda Chemical Industries, Ltd., average pore size: 35 Å)] (20 g) was filled in a 200 ml-volume stainless steel-made cylinder and vacuum-dried. Then, about 80 g of the crude 1,1-difluoroethane of Raw Material Example 2 was filled while cooling the cylinder and occasionally stirred while keeping the temperature at 10° C. After about 20 hours, the liquid phase part was analyzed by gas chromatography and found to have the following composition.

| | | | |
|---|---|---|---|
| $CH_3CHF_2$ | 99.9694 | $CH_2=CH_2$ | 0.0006 |
| $CH_2=CHF$ | 0.0081 | $CH_3CHClF$ | 0.0008 |
| $CH_2=CHCl$ | 0.0166 | $CH_3CHClF$ | 0.0044 |
| $CH_2=CCl_2$ | 0.0001 | | |

(unit: vol %)

As apparent from these results, when an activated carbon having a large pore size is used, the impurities cannot be selectively adsorbed and removed.

EXAMPLE 7

Preparation Example of Crude 1,1-Difluoroethane

Raw Material Example 3

1,1-Dichloroethane and hydrogen fluoride were introduced into an inconel-made reactor filled with a catalyst (mainly comprising trivalent chromium oxide) and reacted at a reaction temperature of 200° C., the resulting reaction gas mainly comprising 1,1-difluoroethane, hydrogen chloride and unreacted hydrogen fluoride was introduced into a first distillation tower, hydrogen chloride which is a low boiling fraction was mainly separated from the top and a side-cut fraction mainly comprising crude 1,1-difluoroethane was separated and withdrawn from a stage upper than the middle portion of the distillation tower. The obtained crude 1,1-difluoroethane had the following composition.

| | | | |
|---|---|---|---|
| $CH_3CHF_2$ | 99.1938 | $CH_2=CH_2$ | 0.0004 |
| $CH_2=CHF$ | 0.0019 | $CH_2=CClF$ | 0.0005 |
| $CH_2=CHCl$ | 0.0018 | $CH_3CHClF$ | 0.0002 |
| $CH_3CH_2Cl$ | 0.0002 | $CH_2=CCl_2$ | 0.0004 |
| HCl | 0.2188 | HF | 0.5820 | unit: vol %

EXAMPLE 8

Preparation Example of Crude 1,1-Difluoroethane

Raw Material Example 4

1,1-Dichloroethane and hydrogen fluoride were introduced into an inconel-made reactor filled with a catalyst (mainly comprising trivalent chromium oxide) and reacted at a reaction temperature of 250° C., the resulting reaction gas, mainly comprising 1,1-difluoroethane, hydrogen chloride and unreacted hydrogen fluoride, was introduced into a first distillation tower, hydrogen chloride which is a low boiling fraction was mainly separated from the top, and hydrogen fluoride, 1,1-difluoroethane, 1,1-dichloroethane and 1-chloro-1-fluoroethane were mainly separated from the bottom and introduced into a second distillation tower. In the second distillation tower, crude 1,1-difluoroethane mainly comprising 1,1-difluoroethane was obtained from the top and hydrogen fluoride, 1,1-dichloroethane and 1-chloro-fluoroethane were mainly separated from the bottom and recirculated to the above-described reaction step. The obtained crude 1,1-difluoroethane had the following composition.

| | | | |
|---|---|---|---|
| $CH_3CHF_2$ | 99.7098 | $CH_2=CH_2$ | 0.0002 |
| $CH_2=CHF$ | 0.0011 | $CH_2=CClF$ | 0.0010 |
| $CH_2=CHCl$ | 0.0008 | $CH_3CHClF$ | 0.0002 |
| $CH_3CH_2Cl$ | 0.0001 | $CH_2=CCl_2$ | 0.0002 |
| HCl | trace amount | HF | 0.2866 | unit: vol %

EXAMPLE 9

Preparation Example of Catalyst

Catalyst Example 1

Pure water (0.6 L) was charged into 10 L-volume container and stirred and, thereto, a solution obtained by dissolving 452 g of $Cr(NO_3)_3 \cdot 9H_2O$ and 42 g of $In(NO_3)_3 \cdot nH_2O$ (n is about 5) in 1.2 L of pure water and 0.31 L of a 28% aqueous ammonia were added dropwise over about 1 hour while controlling the flow rates of two aqueous solutions so that the pH of the reaction solution fell in the range from 7.5 to 8.5. The obtained slurry was separated by filtration and the solid matter separated by filtration was thoroughly washed with pure water and then dried at 120° C. for 12 hours. The dried solid matter was ground, then mixed with graphite and formed into pellets by a tablet making machine.

The produced pellets were baked at 400° C. for 4 hours in a nitrogen stream to obtain a catalyst precursor. This catalyst precursor was filled in an inconel-made reactor and subjected to a fluorination treatment (activation of catalyst) at 350° C. by using hydrogen fluoride to prepare a catalyst.

EXAMPLE 10

Preparation Example of Catalyst

Catalyst Example 2

Chromium chloride ($CrCl_3 \cdot 6H_2O$) (191.5 g) was charged into 132 mL of pure water and dissolved under heating at 70 to 80° C. on a water bath. After cooling the resulting solution to room temperature, 400 g of active alumina (NST-7, produced by Nikki-Universal Co., Ltd.) was added to allow the entire amount of catalyst solution to be absorbed into the alumina. The alumina wetted with the catalyst solution was dried at 90° C. on a water bath and thereby exsiccated. The exsiccated catalyst was dried at 110° C. for 3 hours in an air-circulating hot-air dryer, the dried catalyst was filled in an SUS-made vessel, and the temperature was elevated to 400° C. under circulation of air to produce a catalyst precursor. Thereafter, the fluorination treatment of catalyst (activation of catalyst) was performed by using the same procedure and conditions as in Example 6 to prepare a catalyst.

EXAMPLE 11

Preparation Example of Catalyst

Catalyst Example 3

A catalyst was prepared by the same procedure and operations as in Example 10 except for adding 16.6 g of zinc chloride ($ZnCl_2$) as a second component in Example 10.

EXAMPLE 12

The catalyst (80 mL) obtained in Example 9 (Catalyst Example 1) was filled in an inconel 600-type reactor having an inner diameter of 1 inch and a length of 1 m, the reactor temperature was elevated to 160° C. while passing a nitrogen gas, the crude 1,1-difluoroethane obtained in Example 7 (Raw Material Example 3) was fed at a flow rate of 10 NL/h, the supply of nitrogen gas was stopped and, after 2 hours, the reactor outlet gas was subjected to removal of acid content with an aqueous alkali solution and then analyzed by gas chromatography. As a result, the gas was found to have the following composition.

| $CH_3CHF_2$ | 99.9966 | $CH_2=CH_2$ | 0.0001 |
|---|---|---|---|
| $CH_2=CHF$ | 0.0001 | $CH_2=CClF$ | 0.0001 |
| $CH_2=CHCl$ | trace amount | $CH_3CHClF$ | 0.0002 |
| $CH_3CH_2Cl$ | 0.0005 | $CH_2=CCl_2$ | trace amount |
| $CH_3CClF_2$ | 0.0004 | $CH_3CHClF$ | 0.0017 |
| $CH_3CCl_2F$ | 0.0003 | | | unit: vol %

As is apparent from these results, about 94% of unsaturated compounds each having two carbon atoms were converted into saturated compounds.

EXAMPLE 13

The catalyst (100 mL) obtained in Example 10 (Catalyst Example 2) was filled in an inconel 600-type reactor having an inner diameter of 1 inch and a length of 1 m, the reactor temperature was elevated to 200° C. while passing a nitrogen gas, the crude 1,1-difluoroethane obtained in Example 8 (Raw Material Example 4) was fed at a flow rate of 10 NL/h while feeding hydrogen fluoride at 2 NL/hr, the supply of nitrogen gas was stopped and, after 3 hours, the outlet gas was subjected to removal of acid content with an aqueous alkali solution and then analyzed by gas chromatography, as a result, the gas was found to have the following composition.

| $CH_3CHF_2$ | 99.9984 | $CH_2=CHF$ | 0.0001 |
|---|---|---|---|
| $CH_2=CHCl$ | 0.0001 | $CF_3CHClF$ | 0.0001 |
| $CH_3CH_2Cl$ | 0.0003 | $CH_3CClF_2$ | 0.0009 |
| $CH_3CCl_2F$ | 0.0001 | | | unit: vol %

As apparent from these results, about 94% of the unsaturated compounds were converted into saturated compounds.

The gas above after the passing of an aqueous alkali solution was dehydrated with zeolite, collected into a pressure vessel while cooling and introduced into a third distillation tower, the low boiling fraction was cut from the top, the bottom fraction was introduced into a fourth distillation tower, and 1,1-difluoroethane was recovered from the top and analyzed by gas chromatography, as a result, this gas was found to have a purity of 99.999 vol % or more and an unsaturated compound content of 2 vol ppm or less.

EXAMPLE 14

A reaction was performed by using the same operations and conditions as in Example 13 except for filling 100 mL of the catalyst obtained in Example 11 (Catalyst Example 3). The outlet gas was subjected to removal of acid content with an aqueous alkali solution and then analyzed by gas chromatography, as a result, the gas was found to have the following composition.

| $CH_3CHF_2$ | 99.9985 | $CH_2=CHF$ | 0.0001 |
|---|---|---|---|
| $CH_2=CHCl$ | 0.0002 | $CF_3CHClF$ | 0.0001 |
| $CH_3CH_2Cl$ | 0.0002 | $CH_3CClF_2$ | 0.0008 |
| $CH_3CCl_2F$ | 0.0001 | | | unit: vol %

INDUSTRIAL APPLICABILITY

The present invention makes it possible to produce high-purity 1,1-difluoroethane usable as a cryogenic refrigerant, or as an etching gas, in an industrially advantageous manner.

The invention claimed is:

1. A method for purifying 1,1-difluoroethane, comprising bringing crude 1,1-difluoroethane containing at least one compound selected from the group consisting of unsaturated compounds each having two carbon atoms within the molecule and saturated chlorine-containing compounds each having two carbon atoms within the molecule, into contact with an adsorbent comprising a zeolite having an average pore size of 3 to 6 Å and a silica/aluminum ratio of 2.0 or less and/or a carbonaceous adsorbent having an average pore size of 3.5 to 6 Å.

2. The method for purifying 1,1-difluoroethane as claimed in claim 1, wherein the unsaturated compound having two carbon atoms within the molecule is at least one compound selected from the group consisting of ethylene, fluoroethylene, vinyl chloride and vinylidene chloride.

3. The method for purifying 1,1-difluoroethane as claimed in claim 1, wherein the saturated chlorine-containing compound having two carbon atoms within the molecule is at least one compound selected from the group consisting of dichloroethane, 1-chloro-1-fluoroethane and 2-chloro-1,1,1,2-tetrafluoroethane.

4. The method for purifying 1,1-difluoroethane as claimed in claim 1, wherein the total content of said compounds contained as impurities in the crude 1,1-difluoroethane is 0.1 vol % or less.

5. The method for purifying 1,1-difluoroethane as claimed in claim 1, wherein the pressure for bringing the crude 1,1-difluoroethane into contact with said adsorbent is 1 MPa or less.

6. The method for purifying 1,1-difluoroethane as claimed in claim 1, wherein the total content of said compounds contained as impurities in the purified 1,1-difluoroethane is 100 vol ppm or less.

7. The method for purifying 1,1-difluoroethane as claimed in claim 1, wherein the total content of unsaturated compounds each having two carbon atoms within the molecule, contained as impurities in the purified 1,1-difluoroethane is 50 vol ppm or less.

8. The method for purifying 1,1-difluoroethane as claimed in claim 1, wherein the total content of saturated chlorine-containing compounds each having two carbon atoms within the molecule, contained as impurities in the purified 1,1-difluoroethane is 50 vol ppm or less.

9. The method for purifying 1,1-difluoroethane as claimed in claim 1, wherein the crude 1,1-difluoroethane is obtained by a method comprising the following steps (1) to (3):
   (1) a step of reacting 1,1-dichloroethane with hydrogen fluoride in the presence of a fluorination catalyst to obtain a product containing 1,1-difluoroethane,
   (2) a step of separating hydrogen fluoride, 1,1-dichloroethane and 1-chloro-1-fluoroethane from the product containing 1,1-difluoroethane obtained in the step (1) and circulating the separated compounds to a reaction step, and
   (3) a step of separating, by distillation, hydrogen chloride and 1,1-difluoroethane from the product containing 1,1-difluoroethane obtained in the step (1).

* * * * *